(12) United States Patent
Subramaniam et al.

(10) Patent No.: US 9,044,488 B2
(45) Date of Patent: Jun. 2, 2015

(54) MEDICINAL CREAM MADE USING SILVER SULPHADIAZINE AND CHITOSAN AND A PROCESS TO MAKE IT

(76) Inventors: Vanangamudi Sulur Subramaniam, Chennai (IN); Srinivasan Madhavan, Chennai (IN); Neelakandan Narayanan Chulliel, Chennai (IN); Kuppusamy Senthilkumar, Chennai (IN)

(*) Notice: Subject to any disclaimer, the term of this patent is extended or adjusted under 35 U.S.C. 154(b) by 902 days.

(21) Appl. No.: 13/263,848

(22) PCT Filed: Apr. 5, 2010

(86) PCT No.: PCT/IB2010/051465
§ 371 (c)(1),
(2), (4) Date: Apr. 5, 2012

(87) PCT Pub. No.: WO2010/119369
PCT Pub. Date: Oct. 21, 2010

(65) Prior Publication Data
US 2014/0274943 A1    Sep. 18, 2014

(30) Foreign Application Priority Data
Apr. 13, 2009   (IN) .......................... 961/MUM/2009

(51) Int. Cl.
| A61K 31/555 | (2006.01) |
| A61K 31/722 | (2006.01) |
| A61K 9/00 | (2006.01) |
| A61K 31/635 | (2006.01) |
| A61K 47/36 | (2006.01) |

(52) U.S. Cl.
CPC .............. *A61K 31/555* (2013.01); *A61K 9/0014* (2013.01); *A61K 31/635* (2013.01); *A61K 47/36* (2013.01); *A61K 31/722* (2013.01)

(58) Field of Classification Search
None
See application file for complete search history.

(56) References Cited

U.S. PATENT DOCUMENTS 6,379,702 B1    4/2002   Lorenz

FOREIGN PATENT DOCUMENTS

| CN | 101 596 310 | 12/2009 |
| GB | 2 327 344 | 1/1999 |
| WO | WO 2010/109417 | 9/2010 |

OTHER PUBLICATIONS

References Which Form a Part of the ISR Report Are Not Repeated Here.

*Primary Examiner* — Layla Bland

(57) ABSTRACT

The present invention is directed to a composition for treating bacterial skin infections, along with skin rejuvenation. More particularly, the present invention relates to a pharmaceutical cream comprising a biopolymer, and an antibacterial active ingredient. It discloses a composition for treating fungal skin infections along with skin rejuvenation containing a) a biopolymer in the form of chitosan, b) an active pharmaceutical ingredient (API) composition in the form of silver sulphadiazine used in treating bacterial skin infections, c) a cream base containing primary and secondary emulsifiers, waxy materials, co-solvents, acids, preservatives, buffering agents, anti oxidants, chelating agents, and humectants and d) water. The active ingredients, namely chitosan, and an anti bacterial agent in the form of silver sulphadiazine, are incorporated in cream base for use in treating bacterial skin infections with allergy & itching, & wounds on human skin involving contacting human skin with the above identified composition.

9 Claims, 1 Drawing Sheet

MEDICINAL CREAM MADE USING SILVER SULPHADIAZINE AND CHITOSAN AND A PROCESS TO MAKE IT

FIELD OF INVENTION

The present invention relates to a composition for treating bacterial skin infections along with skin rejuvenation. More particularly, the present invention relates to a pharmaceutical cream comprising a biopolymer, and an antibacterial active ingredient in the form of Silver Sulphadiazine.

BACKGROUND OF THE INVENTION

Skin disorders can be broadly categorized as those arising from bacterial forms or fungi. Antifungal or antibacterial compositions are traditionally applied as lotions, creams or ointments. Furthermore in many instances, it is difficult to ascertain whether the skin condition is due to a bacterial agent or a fungus.

One approach to treating skin disorders is through elimination by trial and error. Antibacterial or antifungal compositions are applied in turn and response monitored and treatment modified. A major disadvantage of this approach is that treatment needs to be applied many times a day during the treatment period. This is greatly inconvenient and also not cost effective for a majority of human population, particularly in the under-developed nations.

There are several treatments available to treat skin disorders caused by bacteria or fungii. Typically, such compositions use steroids, antibacterial agents or antifungal agents, (or a fixed dose combination of these) and focus on these pharmaceutically active ingredients. The composition of such formulations is such as to enhance their physical/chemical/bio-release profile.

Many skin disorders caused by inflammation and bacterial attacks lead to itching and subsequent scratching, which, among other causes, can in turn lead to serious and complicated secondary infections. The conventionally available treatments do not focus on skin healing or rejuvenation; normally these two aspects are left to heal naturally.

The word healing as related to compromised skin conditions (cuts, wounds, infections, inflammations, abrasions, etc.) are not only about prevention, control, elimination of the source cause such as bacteria or fungi but also to restore the skin to its pre-infection state.

The current approaches of skin treatment can be broadly categorized into two stages, a. healing, and b. restoration of skin to pre-ailment state. The healing part comprises elimination, to the best possible extent, of the root cause of the disorder. This may be elimination of bacteria or fungi causing the infection through a suitable treatment of antibacterial or antifungal agents or reducing the inflammation through steroid treatment. While this treatment is under way, the ongoing compromised condition of the skin continues to be susceptible to secondary infections which can be of quite serious nature. In the case of scratched or wounded skin, it is important for blood clotting to occur quickly as it reduces chances of secondary infections. The focus of such treatments, which are administered through creams, lotions, ointments is on the action of active pharmaceutical ingredients. Cream bases or ointment bases are merely viewed as carriers to take APIs to the sites of disorder.

However, the aspect of restoring the skin back to its pre-disorder state is almost completely left to nature. Therefore one key drawback of the existing skin treatment approaches is that they run the risk of secondary infections due to slow blood clotting and wound healing process.

Furthermore, from the study of the prior art several lacking aspects of the existing prescription derma products used for topical treatment of skin disorders. This is manifested by the fact that the cream base matrix or the ointment base has been overlooked for any potential therapeutic benefits. In particular none of the available prior art suggests that:

Topical skin formulations can deliver skin healing or regeneration beyond the activity of the main APIs such that the therapeutic outcome of the main APIs is enhanced.

The addition of biologically active polymers (the so-called biopolymers) is a complex process in which the stability of the formulations could be compromised if the right biopolymer or naturally interacting formulation excipients or process parameters are not well thought through and optimized to enhance and complement therapy outcomes at the drug design stage itself.

Incorporation of a functionally bio-active excipient polymer in cream matrix while retaining the functional stability of the API in a single dose format of dermaceutical cream involves resolution of problems specific to the physical stability of cream matrix.

A look at some of the existing patents illustrates the above points.

U.S. Pat. No. 4,803,066 discloses pharmaceutical compositions which are suitable for topical application in the treatment of bacterial and/or fungal infections. The compositions comprise an apparently synergistic mixture of a silver compound and an azole derivative together with a pharmaceutically acceptable carrier therefor. It has been claimed that the compositions may be applied topically in the treatment of burns ulcers and other skin lesions, general skin infections and also in the treatment of infections of the mucous membranes. Preferred compositions according to the application contained silver sulphadiazine and clotrimazole or metronidazole. The patent document also suggests that the compositions may be applied as ointments, gels, pessaries, tablets and the like. At the time of the application of U.S. Pat. No. 4,803,066, the antimicrobial effect of silver ions was well known. However, some authorities believed that resistant organisms may arise and that it would be advantageous to include a second antimicrobial agent along with the silver salt. The inventors of the products disclosed in U.S. Pat. No. 4,803,066 found that by including an azole derivative with a silver salt in a pharmaceutical composition a synergistic antibacterial and antifungal effect is achieved against several important pathogenic organisms. The use of an azole derivative gives an added advantage that the composition may be used against topical fungal infections as well as against topical bacterial infections.

The U.S. Pat. No. 4,460,369 discloses an adhesive-coated liquid-impervious moisture-vapour-permeable thin polymer sheet suitable as a wound covering has an antibacterial, preferably a solid such as silver sulphadiazine, disseminated throughout the adhesive layer, usually in amounts up to 15 wt. %, to provide uniform antibacterial properties over the wound and surrounding skin areas. The problems with bandages have been described as although these are effective in keeping from the wound or surgical site airborne bacteria, there remains the problem of any bacteria which happen to be present in the site or, more commonly, upon the surrounding skin. In the enclosed conditions provided by bandages, such bacteria can multiply unduly and lead to an infection problem. It has been proposed to overcome this by liberal application of bacteriocidal or bacteriostatic cream or like formulation over and around the wound or surgical site. There are, however, disadvantages in this procedure since the film, if subsequently applied over this moist cream base layer, can corrugate with movement of the body and generally does not adhere.

The U.S. Pat. No. 4,460,369 is based upon the realisation that a bacteriostatic or bacteriocidal material can be incorporated into the adhesive layer of the sheet.

The U.S. Pat. No. 4,460,360 accordingly discloses an adhesive-coated sheet material which is liquid-impervious but has a high moisture-vapour permeability whereby it is apparently suitable as a wound or burn dressing, or surgical drape or like wound-covering material, wherein the adhesive coating has disseminated throughout its mass an amount of an antibacterial material sufficient to kill bacteria in the wound and surrounding covered skin area.

As well as preserving adhesion and avoiding corrugation, this invention has apparently two advantages. Firstly, the antibacterial substance being disseminated throughout the adhesive is present in uniform known amount per unit area both over the wound and over its surroundings. Secondly, no additional substrate is needed so that the sheet can be accurately emplaced on the skin. As already stated, it then lies flat on the skin with consequent uniform water vapour transmission and bacterial barrier properties. Also avoidance of corrugations allows retention of protective and healing wound exudate over burns.

These sample cases are sufficient to give a reasonable picture of the way the silver sulphadiazine has been used in the industry.

None of the above mentioned patent applications teach or suggest together:
  Use of the cream base matrix as a functional element of the cream rather than a mere carrier for the main APIs
  Use a known bio-polymer as a functional excipient along with Silver Sulphadiazine
  Providing far superior healing effects as micro-film forming, blood clotting, supporting epidermal growth, microbial electrostatic immobilization take effect simultaneously rather than one after the other as would be the case in conventional single-drug therapy
  Improve overall medicinal properties of the cream, complimenting the API used in the cream matrix There is therefore a need for a single-dose API topical treatment that will be provided in a cream base, which cream base provides therapeutical value complementary to that provided by the main APIs and serves the purpose over and above that of being a mere carrier or delivery mechanism.

OBJECTS AND ADVANTAGES OF THE INVENTIONS

There is therefore a need to provide a single dose Silver Sulphadiazine topical treatment formulation that will provide an effective treatment against bacterial infections and also help actively heal the skin rejuvenate.

Further objects of the present invention are to provide topical skin treatment formulations that:
  Can deliver skin healing or regeneration beyond the activity of Silver Sulphadiazine such that the therapeutic outcome of the main API is enhanced.
  Contain biologically active polymers (the so-called biopolymers) without compromising the stability of the formulations could be compromised if the right biopolymer is not selected.
  Incorporate a functionally bio-active excipient polymer in cream matrix while retaining the functional stability of the API in a single dose format

SUMMARY OF THE INVENTION

Figure 1:
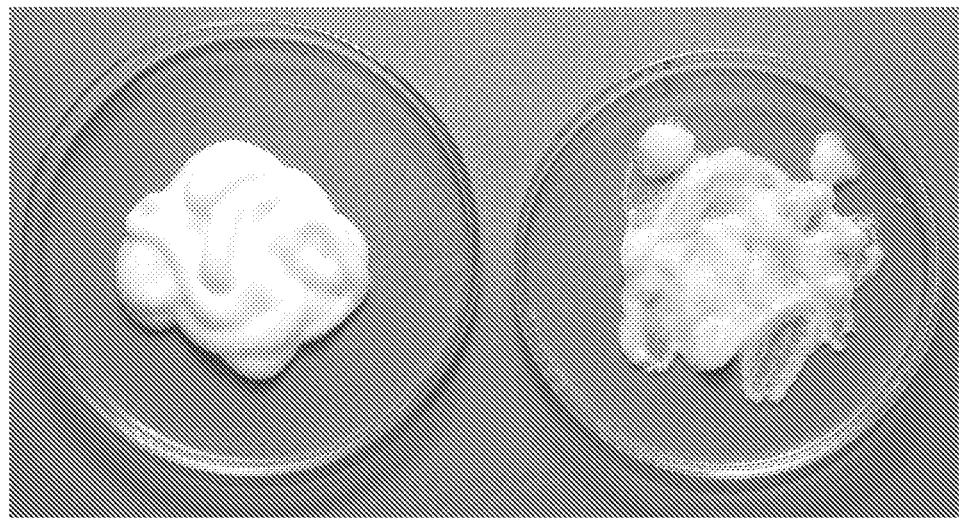
FIG. 1—Non-homogeneous nature of creams containing chitosan with non-compatible excipient such as carbomer FIG. 2—Film formation using chitosan

The present invention is directed to a composition for treating bacterial skin infections along with skin rejuvenation containing
a) a biopolymer in the form of Chitosan
b) An Active Pharmaceutical Ingredient (API) Silver Sulphadiazine used in treating bacterial skin infections.
c) A cream base containing primary and secondary emulsifiers, waxy materials, co-solvents, acids, preservatives, buffering agents, anti oxidants, chelating agents, and humectants.
d) Water The active ingredients, namely chitosan, and Silver Sulphadiazine, are incorporated in cream base for use in treating bacterial skin infections with allergy & itching, & wounds on human skin involving contacting human skin with the above identified composition.

DETAILED DESCRIPTION OF THE INVENTION

Other than in the operating examples, or where otherwise indicated, all numbers expressing quantities of ingredients are understood as being modified in all instances by the term "about".

The present invention provides a uni-dose Silver Sulphadiazine formulation for topical skin treatment in the field of prescription medicaments. The prescription medication is distinct in its use as compared with the so-called cosmeceuticals. The cosmeceuticals are aimed towards beautification or betterment of a more-or-less intact skin or of a skin not suffering from a serious disorder. On the other hand, prescription skin formulations are aimed to provide treatment for serious skin disorders resulting from infections and wounds.

From the study of the prior art several lacking aspects of the existing topical treatment formulations in the field of prescription medications are evident. The prior art does not teach or suggest that:
  Topical skin formulations can deliver skin healing or regeneration beyond the activity of the main APIs such that the therapeutic outcome of the main APIs is enhanced.
  The addition of biologically active polymers (the so-called biopolymers) is a complex process in which the stability of the formulations could be compromised if the right biopolymer is not selected.
  Incorporation of a functionally bio-active excipient polymer in cream matrix while retaining the functional stability of the API in a single dose format of dermaceutical cream involves resolution of problems specific to the physical stability of cream matrix.

The active compound Silver Sulphadiazine which may be employed in the present invention is well known in the art of treatment of bacterial infections, and a bio polymer for treating wounds and rejuvenating human skin involving contacting human skin with the above identified composition.

Examples of suitable biopolymer, which may be used, include, but are not limited to chitosan and the like.

Examples of suitable topical antibacterial agents, which may be used, include, but are not limited to, Sodium Fusidate, Calcium Mupirocin, Gentamycin, Neomycin, Silver Sulphadiazine, Ciprofloxacin, Framycetin Sulphate, Quinidochlor, Povidone-Iodine, Sisomicin, Nitrofural and the like.

This active compound Silver Sulphadiazine require a base component to be used in the pharmaceutical composition that uses the compounds, since the compounds cannot, by themselves, be deposited directly on to human skin due to their harshness.

The base component usually contains primary and secondary emulsifiers, waxy materials, co-solvents, acids, preservatives, buffering agents, anti oxidants, chelating agents, humectants and the like.

Chitosan

Chitosan is a linear polysaccharide composed of randomly distributed β-(1-4)-linked D-glucosamine (deacetylated unit) and N-acetyl-D-glucosamine (acetylated unit). It is known to have a number of commercial uses in agriculture and horticulture, water treatment, chemical industry, pharmaceuticals and biomedics.

It's known properties include accelerated blood clotting. However, it is not known to a person skilled in the art that chitosan's behaviour with a pharmaceutical active ingredient such as an antibacterial or antifungal agent needs to be treated with caution.

It is known to have film forming, mucoadhesive and viscosity-increasing properties and it has been used as a binder and disintegrating agent in tablet formulations.

Chitosan generally absorbs moisture from the atmosphere/environment and the amount absorbed depends upon the initial moisture content, temperature and relative humidity of the environment.

It is regarded as a non-toxic and non-irritant material. It is biocompatible with both healthy and infected skin and has been shown to be biodegradable as it is derived from shrimps, squids and crabs.

Chitosan due to its unique physical property accelerates wound healing and wound repair. It is positively charged and soluble in acidic to neutral solution. Chitosan is bioadhesive and readily binds to negatively charged surfaces such as mucosal membranes. Chitosan enhances the transport of polar drugs across epithelial surfaces. Chitosan's properties allow it to rapidly clot blood, and it has recently gained approval in the USA for use in bandages and other hemostatic agents.

Chitosan is nonallergenic, and has natural anti-bacterial properties, further supporting its use. As a micro-film forming biomaterial, Chitosan helps in reducing the width of the wound, controls the oxygen permeability at the site, absorbs wound discharge and gets degraded by tissue enzymes which are very much required for healing at a faster rate. It also reduces the itching by providing a soothing effect. It also acts like a moisturizer. It is also useful in treatment of routine minor cuts and wounds, burns, keloids, diabetic ulcers and venous ulcers. Chitosan used in the present invention comes in various molecular weights ranging from 1 kdal to 5000 kdal.

Chitosan is discussed in the USP forum with regard to its functional excipient category. Since chitosan is basically a polymer, it is available in various grades depending upon the molecular weight. The various grades of chitosan include chitosan long chain, chitosan medium chain & chitosan short chain. The grades long, medium & short chain directly correspond to the molecular weight of the chitosan.

Generally the long chain grade has a molecular weight in the range of 500,000-5,000,000 Da, the medium chain grade has a molecular weight in the range of 1,00,000-2,000,000 Da and the short chain grade has a molecular weight in the range of 50,000-1,000,000 Da.

The molecular weight of the chitosan plays an important role in the formulation. Higher molecular weight chitosan imparts a higher viscosity to the system and lower molecular weight chitosan imparts a lower viscosity to the system.

However the medium chain grade chitosan delivered an optimum level of viscosity to the formulation. Since the dosage form is a cream, appropriate levels of viscosity is required to achieve a good spreadability over the skin.

The inventors finalized the chitosan medium chain grade for the present invention since it imparted the required rheologic properties to the cream without compromising the therapeutic activity of both the actives and chitosan. The concentration of chitosan medium chain grade was carefully arrived based on several in house trials and Preclinical animal studies for efficacy.

Topical Antibacterials:

Topical Anti-bacterials are intended to target skin for bacterial infections caused by *Staphylococcus aureus, Staphylococcus epidermidis*, Methicillin-resistance *Staphylococcus aureus* (MRSA) etc.

Anti-bacterials act by inhibiting cell wall synthesis by combining with bacterial ribosomes and interfering with mRNA ribosome combination.

In another hypothesis it is believed that anti-bacterials induce ribosomes to manufacture peptide chains with wrong amino acids, which ultimately destroy the bacterial cell.

Topical antibacterial agents include, but are not limited to, Sodium Fusidate, Calcium Mupirocin, Gentamycin, Neomycin, Silver Sulphadiazine, Ciprofloxacin, Framycetin Sulphate, Quinidochlor, Povidone-Iodine, Sisomicin, Nitrofural and the like.

Silver Sulphadiazine

Silver sulphadiazine is a complex of silver and a sulphonamide, sulphadiazine. It is used to treat bacterial infections, by killing or stopping the growth of the bacteria responsible.

The molecular formula of Silver Sulphadiazine is $C_{10}H_9AgN_4O_2S$, and the molecular weight is 357.14. The chemical name is silver (I) sulfadiazine, 4-amino-N-(2-pyrimidinyl)benzenesulfonamide silver salt. It is a White powder insoluble in cold water.

Pharmacology & Mechanism of Action

Silver sulfadiazine is a sulfa derivative topical antibacterial used primarily as a topical burn cream on second- and third-degree burns. The cream is kept applied to the burned skin at all times, for the duration of the healing period or until a graft is applied. It prevents the growth of a wide array of bacteria, as well as yeast, on the damaged skin. Silver sulfadiazine is typically delivered in a 1% solution suspended in a water-soluble base. The chemical itself is poorly soluble, and has only very limited penetration through the skin.

It is also helpful on other shallow, large-area wounds such as abrasions.

It has a broad spectrum of activity, acting against both gram positive and gram-negative organisms (including pseudomonas).

Silver sulphadiazine slowly releases silver ions when applied topically which, together with sulphadiazine exerts a bactericidal action.

Pharmacokinetics

When applied topically it releases silver ions and free sulphadiazine. Some sulphadiazine may be absorbed systemically.

Indications

Silver sulphadiazine is used as a topical antimicrobial agent for the prevention and treatment of infection in burns. It is used in prevention and treatment of infection in chronic leg ulcers and pressure sores. Silver sulphadiazine is also used in prophylaxis of infection in skin graft donor sites. It is also used in prevention of infection in abrasions, laceration and Minor wounds.

Most of the topical products are formulated as either creams or ointments. A cream is a topical preparation used for application on the skin. Creams are semisolid emulsions, which are mixtures of oil and water in which APIs (Active Pharmaceutical Ingredients) are incorporated. They are divided into two types: oil-in-water (O/W) creams which compose of small droplets of oil dispersed in a continuous water phase, and water-in-oil (W/O) creams which compose of small droplets of water dispersed in a continuous oily phase. Oil-in-water creams are user-friendly and hence cosmetically acceptable as they are less greasy and more easily washed with water. An ointment is a viscous semisolid preparation containing APIs, which are used topically on a variety of body surfaces. The vehicle of an ointment is known as ointment base. The choice of a base depends upon the clinical indication of the ointment, and the different types of ointment bases normally used are:

Hydrocarbon bases, e.g. hard paraffin, soft paraffin

Absorption bases, e.g. wool fat, bees wax

Both above bases are oily and greasy in nature and this leads to the undesired effects like difficulty in applying & removal from the skin. In addition this also leads to staining of the clothes. Most of the topical products are available as cream formulation because of its cosmetic appeal.

The acidic scale of pH is from 1 to 7, and the base scale of pH is from 7 to 14. Human skins pH value is some where between 4.5 and 6. Newborn baby's skin pH is closer to neutral (pH 7), but it quickly turns acidic. Nature has designed this probably to protect young children's skin, since acidity kills bacteria. As people become older, the skin becomes more and more neutral, and won't kill as many bacteria as before. This is why the skin gets weak and starts having problems. The pH value goes beyond 6 when a person actually has a skin problem or skin disease. This shows that it is necessary to choose topicals that have a pH value close to that of skin of a young adult.

A slight shift towards the alkaline pH would provide a better environment for microorganisms to thrive. Most of the topical products are available as creams. Active compounds in cream formulations are available in ionized state, whereas in case of ointments these are present in non-ionized state. Generally, the cream formulations are the first choice of the formulators in design and development of topical dosage forms, as the cream formulations are cosmetically elegant, and also as the active compound is available in ionized state, and the drug can penetrate the skin layer fast which makes the formulation totally patient friendly.

The pH of the cream of the present invention with a functional biopolymer such as Chitosan, Framycetin Sulfate is from about 3 to 6. On the other hand, ointments that are commercially available are greasy and cosmetically non elegant. Furthermore, as the active compound in an ointment is in non-ionized form, the penetration of skin is slow.

It is essential that the active drug penetrates the skin for the optimum bio-dermal efficacy. The particle size of the active drug plays an important role here. It is necessary that the active drug is available in colloidal or molecular dispersed state for the product being highly efficacious form. Also this is to be achieved in the safe pH compatible environment of skin (4.0 to 6.0). To achieve all these, it is essential to choose proper vehicles or co-solvents for the dissolution or dispersion of the drug. The product of the present invention is highly efficacious due to the pronounced antibacterial & wound healing activity of Framycetin Sulfate, which is available in ultra micro-size, colloidal form, which enhances skin penetration.

Rationale for the Use of Framycetin Sulfate and Chitosan Combination:

Numerous topical treatments are currently employed for the treatment of bacterial infections. However there is no effective single-dose therapy for protecting the skin, controlling superficial bleeding, wounds and burns. To meet this need and to bring affordable and safe therapy to the dispersed segment of population across all countries/communities, a therapy with unique combination of Chitosan, a biopolymer with skin rejuvenation properties with Framycetin Sulfate is proposed as a novel cream.

Topical Framycetin Sulfate have profound efficacy in primary & secondary bacterial skin infections of varied etiology due to its antibacterial properties. A drawback of the monotherapy with any topical antibacterial has been the relatively slow onset of the effect.

By employing Framycetin Sulfate & chitosan in a formulation, the properties of both antibacterials and chitosan are optimized. As chitosan is film forming, biocompatible, non-allergenic material it helps in protecting the skin by acting as a barrier. It further controls the superficial bleeding caused by scratching and also arrests the mobility of pathogens due to its cationic charge.

The properties of Framycetin Sulfate and chitosan's skin regenerative aspects are well exploited in the present invention and the maximum therapeutic benefit is passed on to the patient thereby aiding in faster healing. This ensures that the patient would benefit for the treatment of skin wounds, burns with bacterial infections.

The inclusion of chitosan in the formulation takes care of many attributes, which are considered to be very much essential in treating skin ailments. The combination of chitosan with Framycetin Sulfate is unique and novel since this is not available commercially across the globe.

The concept of the combination is justified by considering the physical, chemical and therapeutic properties of chitosan used in combination with Framycetin Sulfate.

Inventive Aspects of the Present Invention:

Another inventive aspect of the present invention is that the addition of a functional excipient in the cream base is not a straight forward process of mere addition. The inventor has found that the compatibility of the functional excipient such as chitosan with other agents in the cream is of critical importance. This is because incompatibility would compromise the stability of the final product. As examples, the inventors have found that well known excipients such as Xanthan Gum and carbopol which have been variously used as stabilising agents, cannot be used in combination with functional biopolymers such as chitosan.

Excipients for topical dosage forms include Polymers, Surfactants, Waxy Materials, Emulsifiers etc. Polymers are used as gelling agents, suspending agents, viscosity builders, release modifiers, diluents, etc. Surfactants are used as wetting agents, emulsifiers, solubilising agents release enhancers, etc.

Generally Polymers & Surfactants may or may not possess ionic charge. They may be anionic or cationic or non-ionic in nature. If anionic excipients are included in the formulation they interact with cationic formulation excipients and produce products which are not homogenous, aesthetically not appealing and give rise to unwanted by products, possible allergens, impurities, toxic substances etc due to incompatibility.

Since the dosage is for the treatment of ailing patients, these incompatibilities in the products cannot be accepted and these add more complication to the patients.

The inventors carefully screened the excipients which included the Polymers and Surfactants for developing a formulation. A thorough study was performed after screening the short listed excipients. The possible interactions between the excipients were given much focus and detailed experiments were done.

To quote some examples about the anionic-cationic interaction in the cream dosage form the inventors made some formulations of Framycetin Sulfate (see tables 1-5) containing Xanthan Gum & Chitosan, Acrylic acid polymer & Chitosan, Sodium Lauryl Sulphate & Chitosan, Docusate Sodium & Chitosan and Gum Arabic & Chitosan. The results clearly indicated the occurrence of interactions which was very much visible and seen as lumps into the entire system. The final product was also not aesthetically appealing without homogeneity. The attached FIG. 1 clearly explains the interaction between chitosan and unsuitable anionic excipients. Based on the observations and thorough knowledge about the excipients, the inventors arrived at a robust formula without any possible interactions.

TABLE 1

Formulation of Silver Sulphadiazine Cream with Chitosan and Xanthan Gum

| S. No | Ingredients | % (w/w) |
|---|---|---|
| 1 | Silver Sulphadiazine | 1 |
| 2 | Chitosan | 0.25 |
| 3 | Lactic Acid | 0.1 |
| 4 | Xanthan Gum | 1.0 |
| 5 | White Soft Paraffin | 8.5 |
| 6 | Cetostearyl alcohol | 8.5 |
| 7 | Cetomacrogol 1000 | 2.5 |
| 8 | Methyl Paraben | 0.2 |
| 9 | Propyl Paraben | 0.02 |
| 10 | Light Liquid Paraffin | 5 |
| 11 | Propylene Glycol | 10 |
| 12 | Disodium EDTA | 0.1 |
| 13 | Disodium Hydrogen Orthophosphate | 0.5 |
| 14 | Purified Water | 62.50 |

TABLE 2

Formulation of Silver Sulphadiazine Cream with Chitosan and Acrylic Acid Polymer

| S. No | Ingredients | % (w/w) |
|---|---|---|
| 1 | Silver Sulphadiazine | 1 |
| 2 | Chitosan | 0.25 |
| 3 | Lactic Acid | 0.1 |
| 4 | Acrylic Acid Polymer | 0.75 |
| 5 | White Soft Paraffin | 8.5 |
| 6 | Cetostearyl alcohol | 8.5 |
| 7 | Cetomacrogol 1000 | 2.5 |
| 8 | Methyl Paraben | 0.2 |
| 9 | Propyl Paraben | 0.02 |
| 10 | Light Liquid Paraffin | 5 |
| 11 | Propylene Glycol | 10 |
| 12 | Disodium EDTA | 0.1 |
| 13 | Disodium Hydrogen Orthophosphate | 0.5 |
| 14 | Purified Water | 62.50 |

TABLE 3

Formulation of Silver Sulphadiazine Cream with Chitosan and Sodium Lauryl Sulphate

| S. No | Ingredients | % (w/w) |
|---|---|---|
| 1 | Silver Sulphadiazine | 1 |
| 2 | Chitosan | 0.25 |
| 3 | Lactic Acid | 0.1 |
| 4 | Sodium Lauryl Sulphate | 1.0 |
| 5 | White Soft Paraffin | 8.5 |
| 6 | Cetostearyl alcohol | 8.5 |
| 7 | Cetomacrogol 1000 | 2.5 |
| 8 | Methyl Paraben | 0.2 |
| 9 | Propyl Paraben | 0.02 |
| 10 | Light Liquid Paraffin | 5 |
| 11 | Propylene Glycol | 10 |
| 12 | Disodium EDTA | 0.1 |
| 13 | Disodium Hydrogen Orthophosphate | 0.5 |
| 15 | Purified Water | 62.25 |

TABLE 4

Formulation of Silver Sulphadiazine Cream with Chitosan and Docusate Sodium

| S. No | Ingredients | % (w/w) |
|---|---|---|
| 1 | Silver Sulphadiazine | 1 |
| 2 | Chitosan | 0.25 |
| 3 | Lactic Acid | 0.1 |
| 4 | Docusate Sodium | 1.0 |
| 5 | White Soft Paraffin | 8.5 |
| 6 | Cetostearyl alcohol | 8.5 |
| 7 | Cetomacrogol 1000 | 2.5 |
| 8 | Methyl Paraben | 0.2 |
| 9 | Propyl Paraben | 0.02 |
| 10 | Light Liquid Paraffin | 5 |
| 11 | Propylene Glycol | 10 |
| 12 | Disodium EDTA | 0.1 |
| 13 | Disodium Hydrogen Orthophosphate | 0.5 |
| 14 | Purified Water | 62.50 |

TABLE 5

Formulation of Silver Sulphadiazine Cream with Chitosan and Gum Arabic

| S. No | Ingredients | % (w/w) |
|---|---|---|
| 1 | Silver Sulphadiazine | 1 |
| 2 | Chitosan | 0.25 |
| 3 | Lactic Acid | 0.1 |
| 4 | Gum Arabic | 1.0 |
| 5 | White Soft Paraffin | 8.5 |
| 6 | Cetostearyl alcohol | 8.5 |
| 7 | Cetomacrogol 1000 | 2.5 |
| 8 | Methyl Paraben | 0.2 |
| 9 | Propyl Paraben | 0.02 |
| 10 | Light Liquid Paraffin | 5 |
| 11 | Propylene Glycol | 10 |
| 12 | Disodium EDTA | 0.1 |
| 13 | Disodium Hydrogen Orthophosphate | 0.5 |
| 14 | Purified Water | 62.50 |

The above products (tables 1 to 5) are examples of products that do not form homogeneous creams, and produce non-homogeneous creams of the type illustrated in FIG. 1. Yet the proportions stated in these examples are some things that a person skilled in the art may use based currently available knowledge. Only after a thorough and extensive trials and errors would it be possible to arrive at right types and proportions of excipients.

As we have discussed earlier, in a therapy, Silver Sulphadiazine provide relief against bacterial infections. However, the aspects such as like skin protection, bleeding at the site, mobility of pathogens from one site to another, etc are not addressed so far in a single dose therapy.

This present invention with its single-dose application fills this gap by incorporating chitosan and tapping the required benefits of skin protection (by way of film forming property), stopping the bleeding (by way of blood clotting property) and immobilization of pathogenic microbes (due to its cationic electrostatic property).

Therapeutic value addition by incorporation of a functional excipient in the form of a chitosan which is a biopolymer in the cream matrix. The value addition is an integrated sub-set of the following functional attributes of the biopolymer:
- formulation of a micro-film on the skin surface
- accelerated blood clotting as compared to creams that do not contain film-forming biopolymers
- electrostatic immobilisation of surface microbes due to cationic charge of the biopolymer
- significant enhancement of the skin epithelisation or regeneration The inventive efforts involved in developing the platform technology covered by incorporation of a functional biopolymer in prescription dermaceutical products are:
- in identification of the complementary therapeutic value that such incorporation delivers
- in identification of issues related to physio-chemical stability of the product resulting from the incorporation of the biopolymer
- in providing a single dose format where the bacterial infection has been identified.

The importance of a single dose treatment, particularly in the underdeveloped countries cannot be overemphasized. In absence of access to a general physician in most parts of south Asia or Africa, let alone a skin specialist, a single dose formulation dramatically increases chances of eliminating root cause of the skin disorder while also allowing the skin to regenerate.

During dermatological conditions, currently available therapies do not address the issues like protecting the skin, arresting the bleeding etc. The unique innovative formulation of the present invention takes care of the skin conditions by treating them along with controlling the superficial bleeding at the site. It is well understood that if the superficial bleeding is left untreated, it will lead to secondary microbial infections. The present invention advantageously provides a solution to this unmet need.

Further, with ever increasing pressures on medical support systems and the attendant scarcity/high cost of the same, there is an emergent need all across the globe to address the following issues in such cases—
- Patients waiting too long for treatment
- Staying unnecessarily long when they get to hospital
- Having to come back more often than they need to
- Reducing the length of stay is a key underlying problem to be tackled in most cases. The present invention with its single-dose therapy reduces the overall treatment time of a serious skin disorder significantly.

Preferred Embodiment 1

A novel dermaceutical cream for topical treatment of bacterial skin infections, and for related wound healing, wherein said cream comprises Silver Sulphadiazine, and a biopolymer provided in a cream base, said cream base comprising at least one of each of a preservative, a primary and a secondary emulsifier, a waxy material, a co-solvent, an acid, and water, preferably purified water.

Embodiment No. 1

A novel dermaceutical cream as disclosed in the preferred embodiment no. 1, wherein said cream further comprising any of a group comprising a buffering agent, an antioxidant, a chelating agent, a humectant, or any combination thereof.

Embodiment No. 2

A novel dermaceutical cream as disclosed in the preferred embodiment no. 1 wherein
  said Silver Sulphadiazine is added in an amount between about 0.5% w/w and about 15% w/w, preferably between 0.5 and 5.0% w/w; and, more preferably about 1.0% w/w; and
  said biopolymer is in the form of chitosan, added in an amount between about 0.01% and about 1% by weight, preferably from about 0.01% w/w to about 0.5% w/w and most preferably about 0.25% w/w, said chitosan being US pharmacopeia conformant with regard to its functional excipient category and selected from any grades such as long chain, medium chain & short chain, and has a molecular weight in the range between 50 kDa to 5000 kDa,
  said primary and secondary emulsifiers are selected from a group comprising Cetostearyl alcohol, Cetomacrogol-1000, Cetyl alcohol, Stearyl alcohol, Polysorbate-80, Span-80 and the like and added in an amount from about 1% (w/w) to 20% (w/w); said waxy materials is selected from a group comprising white soft paraffin, liquid paraffin, hard paraffin and the like, or any combination thereof, from about 5% (w/w) to 50% (w/w); said co-solvent is selected from a group comprising Propylene Glycol, Hexylene Glycol, PolyEthylene Glycol-400 and the like, or any combination thereof, and added in an amount from about 5% (w/w) to 50% (w/w); said acid is selected from a group comprising HCl, $H_2SO_4$, $HNO_3$, Lactic acid and the like, or any combination thereof, and added in an amount from about 0.005% (w/w) to 0.5% (w/w); said preservative is selected from a group comprising Methylparaben, Propylparaben, Chlorocresol, Potassium sorbate, Benzoic acid, 2 Phenoxyethanol, Benzyl alcohol and the like, or any combination thereof, and added in an amount from about 0.05% (w/w) to 2.5% (w/w); said water is added in the amount in the range of 20% (w/w) to 85% (w/w), preferably 40% (w/w) to 80% (w/w), more preferably 60% (w/w) to 70% (w/w), preferably purified water.

Embodiment No. 3

A novel cream as disclosed in the preferred embodiment no. 1 and the embodiment no. 2, further comprising a buffering agent which is selected from a group comprising Di Sodium Hydrogen Ortho Phosphate, Sodium Hydrogen Ortho Phosphate, Calcium lactate and the like, or any combination thereof, and added in an amount from about 0.05% (w/w) to 1.00% (w/w).

Embodiment No. 4

A novel cream as disclosed in the preferred embodiment no. 1 and the embodiments no. 2 and 3, further comprising an antioxidant which is selected from a group comprising Butylated Hydroxy Anisole, Butylated Hydroxy Toluene and the like, or any combination thereof, and added in an amount from about 0.05% (w/w) to 5% (w/w).

Embodiment No. 5

A novel cream as disclosed in the preferred embodiment no. 1 and the embodiments no. 2 to 4, further comprising a chelating agent which is selected from a group comprising Disodium EDTA and the like, or any combination thereof, and added in an amount from about 0.05% (w/w) to 1% (w/w).

Embodiment No. 6

A novel cream as disclosed in the preferred embodiment no. 1 and the embodiments no. 2 to 4, further comprising a humectant which is selected from a group comprising Glycerin, Sorbitol, Propylene Glycol and the like, or any combination thereof, and added in an amount from about 5% (w/w) to 50% (w/w).

Embodiment No. 7

A process of making a cream is disclosed, said process comprising the steps of providing Silver Sulphadiazine, and a biopolymer in a cream base comprising at least one of each of a preservative, a primary and a secondary emulsifier, a waxy material, a co-solvent, an acid, and water, preferably purified water, and mixing all the ingredients together to form a homogeneous cream.

Embodiment No. 8

A process of making a cream as disclosed in the embodiment no. 7, wherein the ingredients further comprise any of a group comprising a buffering agent, an antioxidant, a chelating agent, a humectant, a stabilizer or any combination thereof.

Embodiment No. 9

A novel cream as disclosed in any of the foregoing embodiments, wherein chitosan has a molecular weight range of 1 kdal to 5000 kdal.

The present invention will be further elucidated with reference to the accompanying examples containing the composition and stability studies data, which are however not intended to limit the invention in any way whatever.

Example-I

TABLE 6

| S. No | Silver Sulphadiazine 1% + Chitosan Cream | |
|---|---|---|
| | Ingredients | % (w/w) |
| 1 | Silver Sulphadiazine | 1 |
| 2 | Chitosan | 0.25 |
| 3 | Lactic Acid | 0.1 |
| 4 | White Soft Paraffin | 8.5 |
| 5 | Cetostearyl alcohol | 8.5 |
| 6 | Cetomacrogol 1000 | 2.5 |
| 7 | Methyl Paraben | 0.2 |
| 8 | Propyl Paraben | 0.02 |
| 9 | Light Liquid Paraffin | 5 |

TABLE 6-continued

| S. No | Silver Sulphadiazine 1% + Chitosan Cream | |
|---|---|---|
| | Ingredients | % (w/w) |
| 10 | Propylene Glycol | 10 |
| 11 | Disodium EDTA | 0.1 |
| 12 | Disodium Hydrogen Orthophosphate | 0.5 |
| 13 | Purified Water | 63.50 |

A comparison of table 6 with tables 1 to 5 will illustrate the difference in the products that would be based on the conventional drug design and the innovative approach adopted in the present invention.

API-stability experiments were carried out (see tables 7-9) using the product of the present invention. Tests were carried out to observe (or measure as appropriate) the physical appearance of the product, the pH value and assay of the API over a period of time. Each gram of product of the present invention used for the tests contained appropriate amount of antibacterial. The product used for the Stability Studies tests contained approximately 10% extra API (overages). It was packaged in an aluminium collapsible tube.

Detailed test results for the present invention has been presented. The % of the Silver Sulphadiazine used in all examples are measured w/w with respect to the final product.

Product: Silver Sulphadiazine Cream

Pack: Aluminum Collapsible tube

Composition: Each gm contains: i) Silver Sulphadiazine USP 1.0% w/w

TABLE 7

Description Test, Batch No. SSC-10
Measured parameter: Physical appearance
Best value of measured parameter: Homogeneous
White to off White Viscous cream;
Method of measurement: Observation by naked eye

| Conditions | Initial | 1st Month | 2nd Month | 3rd Month |
|---|---|---|---|---|
| 40° C. 75% RH | Homogenous White to off White viscous cream | Homogenous White to off White viscous cream | Homogenous White to off White viscous cream | Homogenous White to off White viscous cream |
| 30° C. 65% RH | | Homogenous White to off White viscous cream | Homogenous White to off White viscous cream | Homogenous White to off White viscous cream |
| 25° C. 60% RH | | Homogenous White to off White viscous cream | Homogenous White to off White viscous cream | Homogenous White to off White viscous cream |
| Temp cycling | | Homogenous White to off White viscous cream | — | — |
| Freezthaw | | Homogenous White to off White viscous cream | — | — |

TABLE 8 pH Test, Batch No. SSC-10
Measured parameter: pH;
Limits of measured parameter: 3-6
Method of measurement: Digital pH Meter

| Conditions | Initial | 1st Month | 2nd Month | 3rd Month |
|---|---|---|---|---|
| 40° C. 75% RH | 5.35 | 5.34 | 5.33 | 5.32 |
| 30° C. 65% RH | — | 5.35 | 5.34 | 5.33 |
| 25° C. 60% RH | — | 5.34 | 5.33 | 5.33 |
| Temperature cycling | — | 5.32 | — | — |
| Freezthaw | — | 5.33 | — | — |

TABLE 9

Assay (%) Test, Batch No. SSC-10
Measured parameter: Assay (%);
Limits of measured parameter: 90-110
Method of measurement: HPLC Method

| Conditions | Initial | 1st Month | 2nd Month | 3rd Month |
|---|---|---|---|---|
| 40° C. 75% RH | 108.37 | 108.26 | 108.22 | 108.18 |
| 30° C. 65% RH | — | 108.35 | 108.33 | 108.22 |
| 25° C. 60% RH | — | 108.34 | 108.30 | 108.28 |
| Temperature cycling | — | 108.11 | — | — |
| Freezthaw | — | 108.08 | — | — |

Method of Application of the Cream:

The cream is applied after thorough cleansing and drying the affected area. Sufficient cream should be applied to cover the affected skin and surrounding area. The cream should be applied two-four times a day depending upon the skin conditions for the full treatment period, even though symptoms may have improved.

Experiments:

Experiments were carried out with the cream in laboratory as well as using suitable animal models inflicted with excision wounds. Four aspects were tested—wound contraction, epithelisation, blood clotting time, and film forming. These aspects together would suggest that the microbes were immobilized thereby leading to effective wound healing.

A. Wound Contraction:

Excision wound healing activity of the cream of the present invention was determined through animal testing. An excision wound 2.5 cm in diameter was inflicted by cutting away full thickness of the skin. The amount of contraction of the wound observed over a period indicated that the cream of present invention provides significantly improved wound contraction than that achieved through application of a conventional cream.

B. Period Of Epithelisation:

Epithelisation of the wound occurred within shorter number of days using the cream of the present invention as compared to the days taken for epithelisation using the conventional cream. Therefore one benefit of the cream of the present invention is that it facilitates faster epithelisation of the skin than through the use of conventional creams.

C. Blood Clotting:

Blood clotting time was observed in both group of animals, untreated control group and the test group of animals treated with the product of the present invention. Statistically significant decrease in the blood clotting time in treated group animals was observed when compared with that of the control group animals. The mean percent reduction of 10-40% was observed for the blood clotting time using the product of the present invention.

Film Forming Properties:

It is evident from FIG. 1 that chitosan does not lose its film forming property in the presence of the excipients used for cream preparations in the present invention.

Results and Discussion:

It is evident that the properties of chitosan when used in formulations containing the excipients used in the current invention are not compromised in any way. This has been achieved through a careful selection of excipients. For example, our experiments show that widely used excipients such as xanthan gum or carbopol precipitate in combination with chitosan due to cationic, anionic interactions.

The therapeutic impact, as observed from the animal testing, of the addition of chitosan to Silver Sulphadiazine is shown in the following table by considering various aspects of therapeutic cure of a compromised skin condition:

TABLE 10

Figure 2:
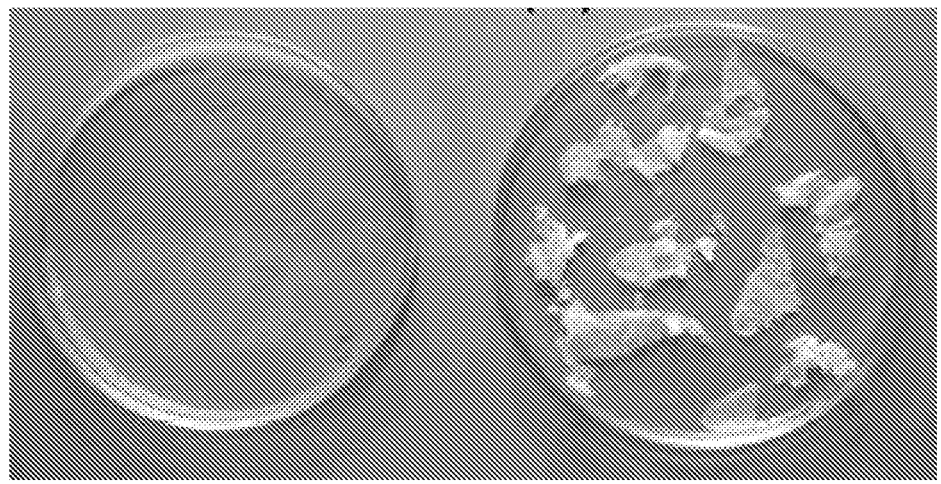

| Therapeutic aspect | Existing creams | Products of the present invention |
|---|---|---|
| 1. Blood Clotting time | None explicitly claimed | Statistically significant reduction in clotting time as evidenced by pre-clinical animal trials |
| 2. Immobilisation of microbes | None explicitly claimed | Expected to immobilise the surface microbes because of the cationic charge of chitosan |
| 3. Epidermal growth support | None explicitly claimed | It is well known that chitosan possesses properties that have significant complimentary action on epidermal growth. This functional aspect of chitosan is preserved in the product of the present invention |
| 4. Micro-film forming | None explicitly claimed | Yes (see FIG. 2) |
| 5. Overall wound healing medicinal effect | Standard as per existing products | Provides superior healing properties |

It is evident that the film forming ability of the chitosan incorporated in the cream allows better access of Silver Sulphadiazine to the infected area and results in better functioning of this API.

The therapeutic efficacy of topically applied cream of the present invention is due to the pronounced antibacterial activity of Silver Sulphadiazine against the organisms responsible for skin infections, the unique ability of actives to penetrate intact skin and wound healing & soothing properties of chitosan.

It is evident from the foregoing discussion that the present invention offers the following advantages and unique aspects over the currently available dermaceutical compositions for bacterial infections:

1. The cream of the present invention incorporates a skin-friendly biopolymer in the form of chitosan provides enhanced therapeutic outcomes. This is evident from the reduced blood clotting time, increased epithelial effect, and faster relief from infection.
2. The cream of the present invention incorporates a biopolymer without compromising the stability of the cream matrix and without adversely affecting the functioning of known active pharmaceutical ingredients. This has been achieved through a careful selection of functional excipients to bypass undesirable aspects of physio-chemical compatibility/stability and bio-release.
3. The cream of the present invention provides an integrated uni-dose or a single-dose therapy hitherto unavailable in prescription dermaceutical formulations.

4. The novel cream of the present invention is adequately stable/efficacious at ambient conditions and does not need special temperature control during transportation/storage—hence will go a long way in achieving these social objectives.

According to another embodiment of the present invention, there is also provided a process for treating bacterial skin infections, and wound healing involving contacting human skin with the above-disclosed composition.

While the above description contains much specificity, these should not be construed as limitation in the scope of the invention, but rather as an exemplification of the preferred embodiments thereof. It must be realized that modifications and variations are possible based on the disclosure given above without departing from the spirit and scope of the invention. Accordingly, the scope of the invention should be determined not by the embodiments illustrated, but by the appended claims and their legal equivalents.

The invention claimed is:

1. A dermaceutical cream for topical treatment of bacterial skin infections and for related wound healing, the cream comprising silver sulphadiazine and chitosan provided in a cream base, the cream base comprising at least one of each of a preservative, a primary and a secondary emulsifier, a waxy material, a co-solvent, an acid, and water.

2. The dermaceutical cream of 1, wherein said cream further comprises an ingredient selected from the group consisting of a buffering agent, an antioxidant, a chelating agent, a humectant, a stabilizer, and any combination thereof.

3. The dermaceutical cream of claim 1 comprising:
   the silver sulphadiazine in an amount between about 0.5% w/w and about 15% w/w;
   the chitosan in an amount between about 0.01% and about 1% by weight;
   the preservative in an amount from about 0.05% (w/w) to about 2.5% (w/w), wherein the preservative is selected from a group comprising methylparaben, propylparaben, chlorocresol, potassium sorbate, benzoic acid, 2-phenoxyethanol, benzyl alcohol and any combination thereof;
   the primary and secondary emulsifiers in an amount from about 1% (w/w) to about 20% (w/w), wherein the primary and secondary emulsifiers are selected from the group consisting of cetostearyl alcohol, cetyl alcohol, stearyl alcohol, and any combination thereof;
   the waxy material in an amount from about 5% (w/w) to about 50% (w/w), wherein the waxy material is selected from the group consisting of white soft paraffin, liquid paraffin, hard paraffin, and any combination thereof;
   the co-solvent in an amount from about 5% (w/w) to about 50% (w/w), wherein the co-solvent is selected from a group comprising propylene glycol, hexylene glycol, polyethylene glycol-400, and any combination thereof;
   the acid in an amount from about 0.005% (w/w) to about 0.5% (w/w), wherein the acid is selected from the group consisting of HCl, $H_2SO_4$, $HNO_3$, lactic acid and any combination thereof; and
   the water in an amount from about 20% (w/w) to 85% (w/w).

4. The dermaceutical cream of claim 1, further comprising a buffering agent in an amount from about 0.05% (w/w) to about 1.00% (w/w), wherein the buffering agent is selected from the group consisting of disodium hydrogen orthophosphate, sodium hydrogen orthophosphate, calcium lactate, and any combination thereof.

5. The dermaceutical cream of claim 1, further comprising an antioxidant in an amount from about 0.05% (w/w) to about 5% (w/w), wherein the antioxidant is selected from the group consisting of butylated hydroxy anisole, butylated hydroxy toluene, and any combination thereof.

6. The dermaceutical cream of claim 1, further comprising disodium EDTA in in an amount from about 0.05% (w/w) to about 1% (w/w).

7. The dermaceutical cream of claim 1, further comprising a humectant in an amount from about 5% (w/w) to about 50% (w/w), wherein the humectant is selected from the group consisting of glycerin, sorbitol, propylene glycol, and any combination thereof.

8. A process for making a dermaceutical cream, the process comprising:
   (a) providing as ingredients:
      (i) silver sulphadiazine;
      (ii) chitosan; and
      (iii) a cream base, the cream base comprising at least one of each of a preservative, a primary and a secondary emulsifier, a waxy material, a co-solvent, an acid, and water; and
   (b) mixing all the ingredients together to form a homogeneous cream.

9. A process of claim 8, wherein the ingredients further comprise an ingredient selected from the group consisting of a buffering agent, art antioxidant, a chelating agent, a humectant, a stabilizer, and any combination thereof.

* * * * *